US00PP19188P2

(12) United States Plant Patent
Lamb et al.

(10) Patent No.: US PP19,188 P2
(45) Date of Patent: Sep. 9, 2008

(54) ***SPATHIPHYLLUM* PLANT NAMED 'SP9028-5'**

(50) Latin Name: ***Spathiphyllum* hybrid**
Varietal Denomination: SP9028-5

(75) Inventors: Ann Elizabeth Lamb, Sebring, FL (US); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/788,171

(22) Filed: Apr. 19, 2007

(51) Int. Cl.
*A01H 5/00* (2006.01)

(52) U.S. Cl. ..... Plt./364

(58) Field of Classification Search ..... Plt./364
See application file for complete search history.

*Primary Examiner*—Annette H Para
(74) *Attorney, Agent, or Firm*—Jondle & Associates, P.C.

(57) ABSTRACT

A new *Spathiphyllum* plant particularly distinguished by attractive, highly branched, dense leafy growth habit, dark green shiny, textured leaves, attractive white, fragrant spathes and good tolerance to environmental extremes without becoming yellow is disclosed.

3 Drawing Sheets

Genus and species: *Spathiphyllum* hybrid.
Variety denomination: 'SP028-5'.

BACKGROUND OF THE NEW PLANT

The present invention comprises a new and distinct cultivar of *Spathiphyllum,* botanically known as *Sphathiphyllum* hybrid, and hereinafter referred to by the cultivar name 'SP9028-5'. The new cultivar originated from a hybridization made in June, 2002 in Apopka, Fla. The female parent was *Spathiphyllum* cv. 'Valentino' (U.S. Plant Pat. No. 13,670). The male parent was *Spathiphyllum* cv. 'Double Take' (U.S. Plant Pat. NO. 12,835).

A single plant selection was chosen for further evaluation and for asexual propagation in March, 2004.

The new cultivar was first propagated in March, 2004 in Apopka, Fla. and has been asexually reproduced repeatedly by tissue culture in Apopka, Fla. over six generations. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Attractive, highly branched, dense leafy growth habit;
2. Dark green shiny, textured leaves.
3. Attractive white, fragrant spathes; and
3. Good tolerance to environmental extremes without becoming yellow.

DESCRIPTION OF PHOTOGRAPHS

This new *Spathiphyllum* plant is illustrated by the accompanying photographs which show overall plant habit including blooms, buds, and foliage of the plant; the colors shown are as true as can be reasonably obtained by conventional photographic procedures.

DESCRIPTION OF THE NEW CULTIVAR

Figure 1:
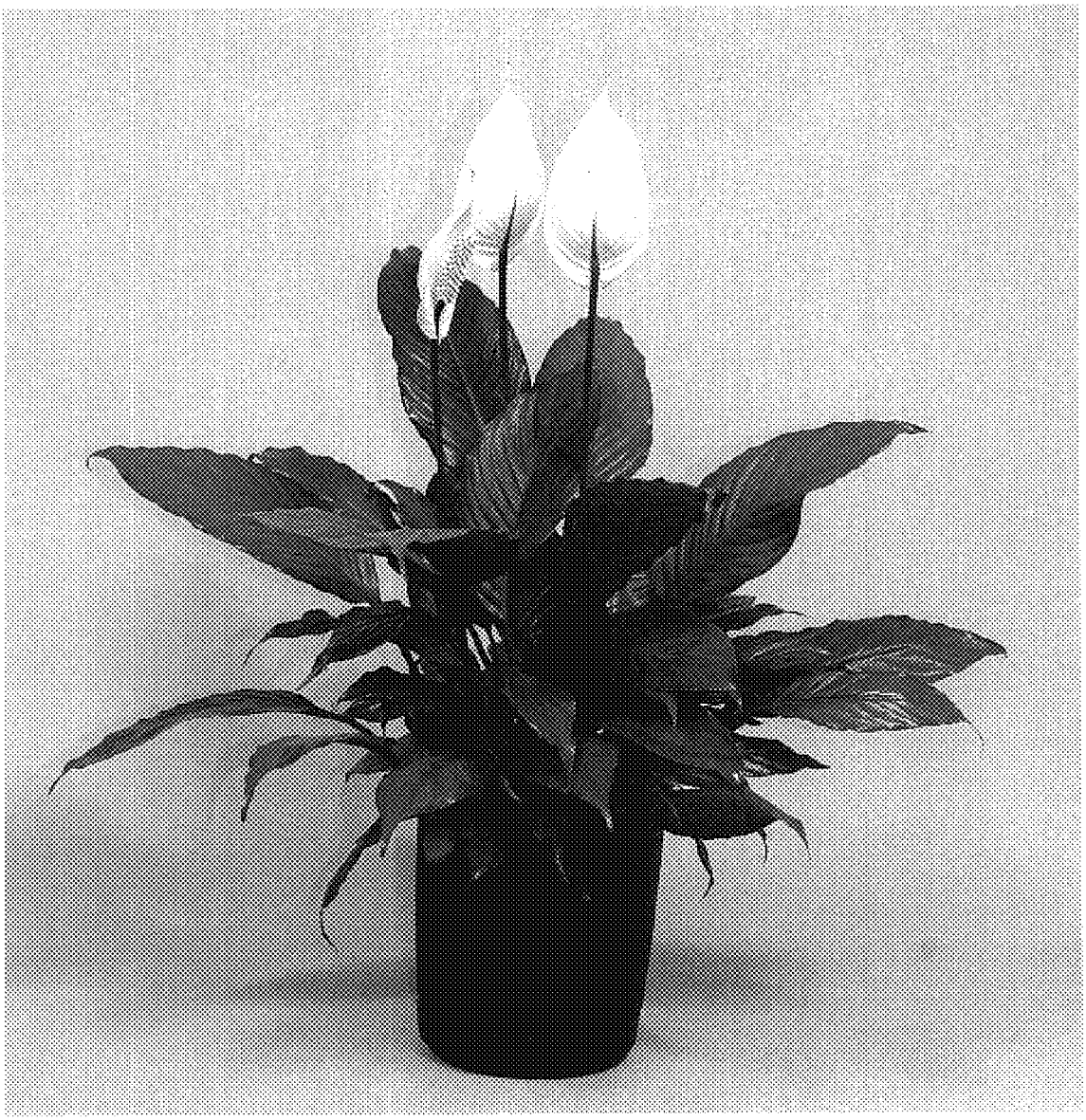
FIG. 1 shows the overall plant habit, including blooms, buds, mature foliage, and plant habit.
Figure 2:
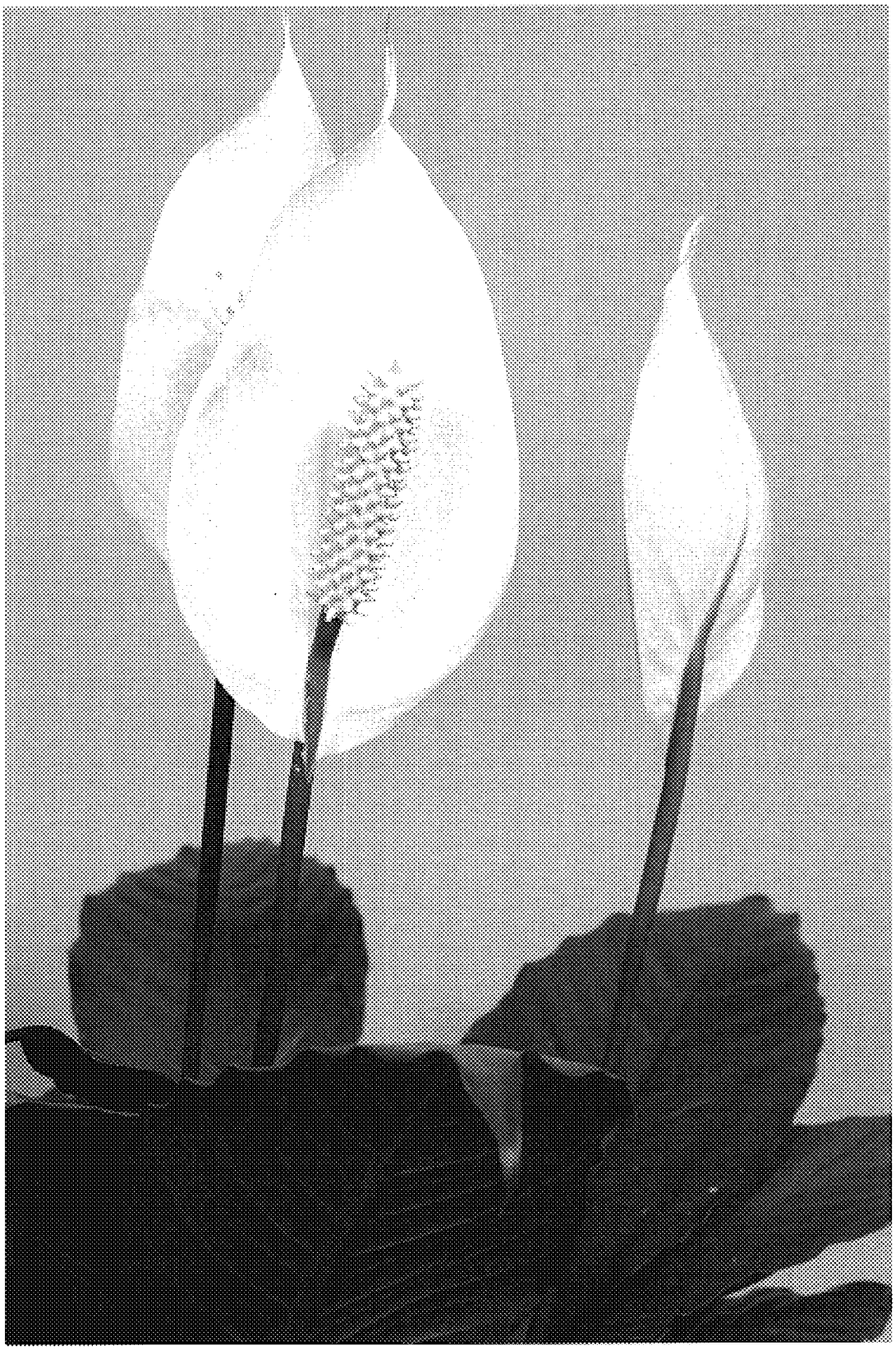
FIG. 2 shows a mature inflorescence.
Figure 3:
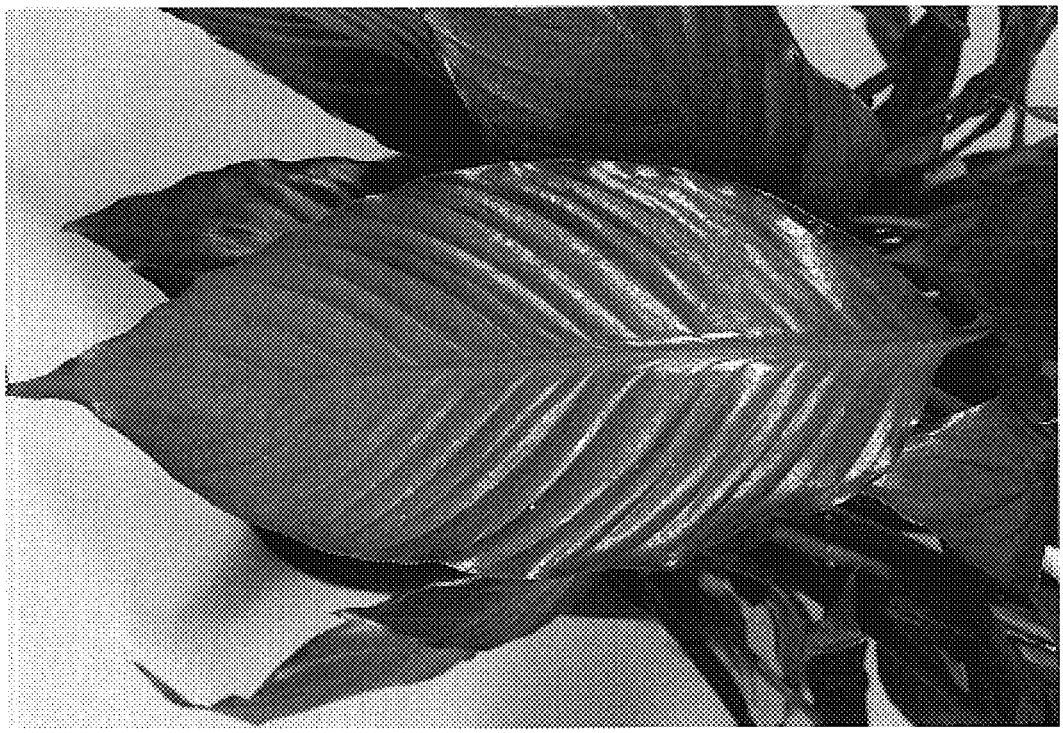
FIG. 3 shows the upper surface of a mature leaf.
Figure 4:
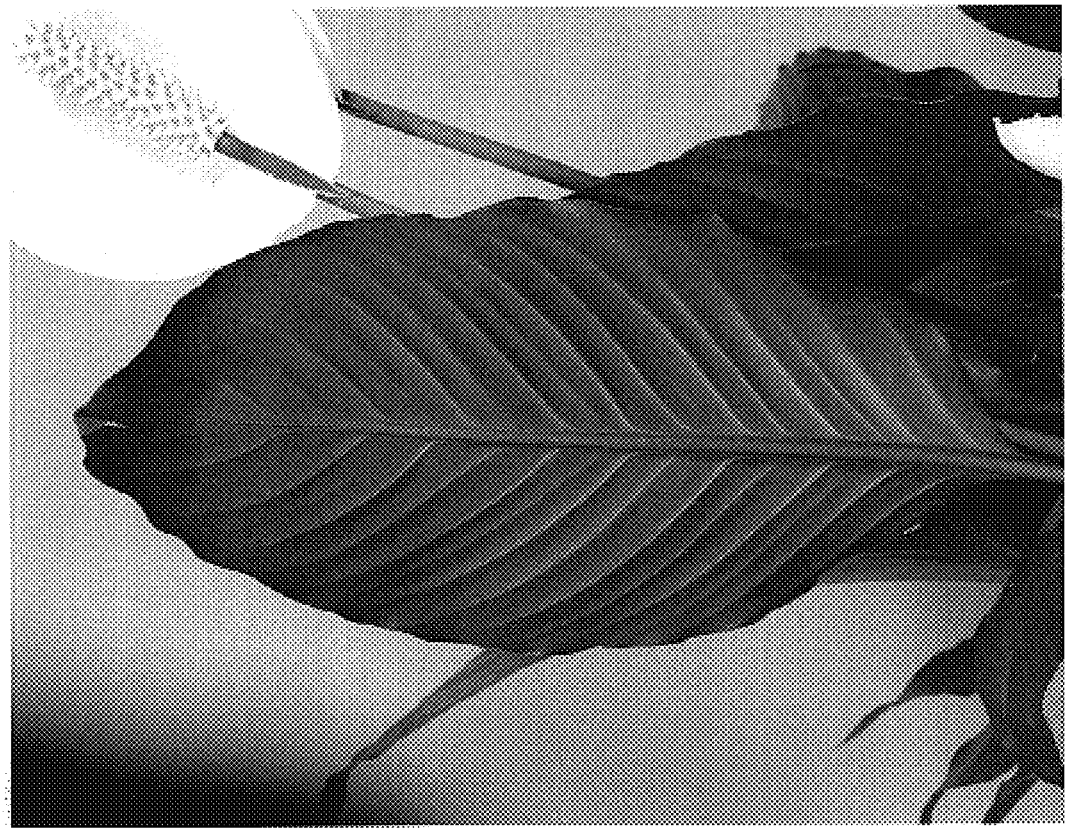
FIG. 4 shows the lower surface of a mature leaf.

The following detailed description sets forth the distinctive characteristics of 'SP9028-5'. The data which define these characteristics were collected from asexual reproductions carried out in Zolfo Springs, Fla. The data were obtained in April 2006 from 7-month-old plants grown in 15-cm to 20-cm pots and started from 70- to 84-day-old liner initiated from a single tissue culture-derived micro-cutting. The plants were grown in a shade-cloth enclosure with a daily temperature range of 75° to 90° F. and a nightly temperature range of 65° to 72° F. The light level was about 2000 foot candles; there were no photoperiodic treatments or growth retardant treatments, however gibberellic acid was used to induce flowering. Color references are to The Royal Horticultural Society Colour Chart, 2001 edition.

DETAILED BOTANICAL DESCRIPTION OF THE NEW PLANT

Classification:
- *Family.*—Araceae.
- *Botanical name.*—*Spathiphyllum* hybrid.
- *Common name.*—Peace lily, white anthurium.

Parentage:
- *Female parent.*—*Spathiphyllum* cv. 'Valentino' (U.S. Plant Pat. No. 13,670).
- *Male parent.*—*Spathiphyllum* cv. 'Double Take' (U.S. Plant Pat. No. 12,835).

Growth:
- *General.*—Tropical flowering potted plant; plant is suitable for use in shaded tropical landscapes and indoors.
- *Time to finish.*—About 7 to 8 months to finish when starting from a 70- to 84-day-old liner initiated from a single tissue culture-derived micro-cutting.
- *Appropriate container.*—15 cm to 20 cm pots; suitable for use in shaded tropical landscapes and indoors.

Plant description:

*Life cycle.*—Herbaceous perennial.

*Habit.*—Upright symmetrical shape; leaves upright when juvenile, arching outward as the plant matures.

*Height, from soil to top of leaf plane.*—32.0 cm to 38.0 cm.

*Height, from soil to top of inflorescence.*—38.0 cm to 45.0 cm.

*Spread.*—50.0 cm to 56.0 cm.

*Vigor.*—Good.

*Roots.*—Thick, fleshy, white, freely branching with fine lateral branches.

*Durability of foliage to stresses.*—Better than average durability when grown indoors; good tolerance to mechanical damage from shipping and handling.

*Temperature tolerances.*—Tolerates high temperatures to about 104° F. and low temperatures to about 45° F. without noticeable damage.

Stems:

*Type.*—Basal branching.

*Number.*—14 basal branches originating from a single micro-cutting.

*Description.*—Ovate to columnar, round in transverse section; leaves arranged in closely spaced vertical ranks.

*Length.*—1.5 cm to 2.8 cm depending upon age of shoot.

*Diameter.*—1.0 cm to 2.5 cm depending upon age of shoot.

*Internode length.*—0.4 cm.

*Aspect.*—Upright.

*Strength.*—Tough, somewhat flexible.

*Color.*—Immature: Outside: RHS 155C (white). Inside: RHS 155C (white). Mature: Outside: RHS 155C (white) tinged with RHS 137C (green) if exposed to light. Inside: RHS 155C (white).

Leaves:

*Arrangement.*—Alternate, simple.

*Number.*—6 to 8 leaves per stem; fewer on younger shoots.

*Shape.*—Ovate to lanceolate.

*Apex.*—Acuminate.

*Base.*—Obtuse to cuneate.

*Margin.*—Entire, wavy.

*Size.*—Length: 20.5 cm to 26.5 cm. Width: 7.2 cm to 10.7 cm.

*Color.*—Immature leaf: Upper surface: Greener than, but closest to RHS 137A. Lower surface: RHS 147B. Mature leaf: Upper surface: Much darker and greener than, but closest to RHS 147A. Lower surface: Darker and greener, but closest to RHS 137B.

*Venation.*—Type: Pinnate; main veins and mid-rib recessed on upper surface and protruding from lower leaf surface. Color: Upper surface: Much darker and greener than, but closest to RHS 147A. Lower surface: Veins RHS 147B; mid-rib RHS 147B to RHS 146C.

*Texture.*—Upper surface: Smooth, shiny; blade convex between main veins giving the leaf a textured appearance. Lower surface: Smooth, glossy.

*Surface pubescence.*—Absent.

Petiole:

*Length.*—19 cm.

*Diameter, distal.*—0.5 cm.

*Diameter, proximal* (*flattened for measurement* ).—6 cm; base of petiole clasps and encircles the stem.

*Aspect.*—Upright when newly emerged becoming about 45 degrees from the vertical axis as more leaves emerge above it.

*Color.*—Much darker and greener than, but closest to RHS 147A.

Geniculum:

*Length.*—4.5 cm.

*Diameter.*—0.48 cm.

*Aspect.*—Straight or slightly curved outward.

*Color.*—Darker and greener than, but closest to RHS 147A.

*Wing length.*—12.0 cm to 14.0 cm.

*Wing diameter.*—1.0 cm at midpoint.

*Wing color.*—Darker and greener than, but closest to RHS 147A.

Peduncle:

*Length, as measured from base of peduncle to base of spathe.*—30.0 cm to 34.0 cm.

*Diameter.*—0.4 cm to 0.6 cm.

*Angle.*—Straight, upright.

*Strength.*—Tough, flexible.

*Color.*—RHS 137A to RHS 147A.

Inflorescence:

*Arrangement.*—Cupped, ovate flower spathe surrounding a columnar spadix borne atop a tall upright peduncle; monoecious; spadix a central column of densely packed, sessile, simple flowers.

*Flowering habit.*—Natural bloom starts in the late winter and repeat flowering occurs for about 3 to 4 months; flowering can be induced by applying gibberellic acid at any time of the year.

*Lastingness of the spathes on the plant.*—About 3 to 4 weeks with good color; spathes become tinged with green as they age; senescence/browning occurs after about 8 to 10 weeks.

*Longevity as a cut flower.*—About 7 days.

*Persistent/self-cleaning.*—Persistent.

*Flowering season.*—Late winter through summer.

*Time to flower.*—Inflorescences initiated about 12 weeks after induction.

*Rate of inflorescence opening.*—About 1 new inflorescence opens every 7 to 10 days.

*Number of inflorescences per plant.*—6.

*Fragrance.*—Sweet perfume.

*Inflorescence height.*—38.0 to 45.0 cm.

*Immature inflorescence* ("*bud*").—Spathe tightly rolled around spadix. Shape: Spindle-shaped. Length: About 9.5 cm. Width: 1.4 cm. Color: Whiter than, but closest to RHS 155A; mid-rib RHS 137B; apex tinged with RHS 143A.

Spathe:

*Arrangement.*—Straight, upright.

*Shape.*—Ovate, cupped.

*Margin.*—Entire.

*Apex.*—Acuminate to acute.

*Base.*—Cuneate to obtuse.

*Length.*—14.0 cm to 16.5 cm.

*Diameter.*—6.5 cm to 8.9 cm.

*Height* (*depth*).—2.0 cm.

*Texture.*—Both sides smooth, slightly glossy.

*Color, when opening.*—Front side: RHS 155D; apex tinged with RHS 143A. Rear side: Whiter than but closest to RHS 155A; mid-rib RHS 137B; apex tinged with RHS 143A.

*Color, when fully opened.*—Front side: paper white; apex tinged with RHS 143A. Rear side: Paper white; mid-rib RHS 137B; apex tinged with RHS 143A.

*Color, fading to.*—After about 3 to 4 weeks, spathes become progressively more tinged with RHS 143B (green) as they age, ultimately becoming RHS N199B with senescence.

Spadix:

*Arrangement.*—Straight, upright.

*Shape.*—Columnar.

*Margin.*—Spadix covered with cone-shaped flower pistils.

*Apex.*—Blunt, rounded.

*Base.*—Obtuse.

*Length.*—5.2 cm to 8.8 cm.

*Diameter.*—1.4 cm to 1.8 cm.

*Color.*—Immature: RHS 157B. Mature: RHS 158C to RHS 158D.

*Flowers.*—Type: Simple, individual flowers reduced to the most basic elements. Shape: Elliptic to ovate, with protruding cone-shaped pistil surrounded by four tepals. Flower diameter: 0.3 cm. Flower height (depth): 0.6 cm to 0.7 cm overall from base to tip; cone-shaped pistil extends about 0.3 cm beyond the male flowers. Number of female flowers per spadix: 112 to 188. Number of male flowers per spadix: 8.

Reproductive Organs:

*Stamens.*—Quantity: 8. Anther length: 0.3 cm to 0.4 cm. Anther color: RHS 158C to RHS 158D. Pollen amount: Moderate to abundant. Pollen color: RHS 155D.

*Pistils.*—Quantity: 112 to 188. Length: 0.6 cm to 0.7 cm. Pistil shape: Cone-shaped. Stigma color: RHS 158C to RHS 158D. Ovary color: RHS 158C to RHS 158D.

Fruit and Seed Set: Has not been observed.

Disease and Insect Resistance: Resistance and susceptibility is typical of the species.

COMPARISON WITH PARENTAL AND COMMERCIAL CULTIVARS

'SP9028-5' differs from the female parent *Spathiphyllum* 'Valentino' (U.S. Plant Pat. No. 13,670) in that 'SP9028-5' has a narrower plant habit than 'Valentino'. In addition, 'SP9028-5' has a shorter peduncle and few spathes than 'Valentino'.

'SP9028-5' differs from the male parent *Spathiphyllum* 'Double Take' (U.S. Plant Pat. No. 12,835) in that 'SP9028-5' has a shorter plant habit and more branches than 'Double Take'. Additionally, 'SP9028-5' has wider, darker green leaves and longer spathes than 'Double Take'.

'SP9028-5' differs from the commercial *Spathiphyllum* variety 'Petite' (unpatented) in that 'SP9028-5' has larger, wider, glossier and more textured leaves than 'Petite'. In addition, 'SP9028-5' has a larger ovate spathe while 'Petite' has a smaller and narrower spathe. 'SP9028-5' forms many branches from a single microcutting allowing a single microcutting to fill a 15 cm to 20 cm pot while 'Petite' requires more than one microcutting to fill a 15 cm to 20 cm pot.

We claim:

1. A new and distinct cultivar of *Spathiphyllum* plant as shown and described herein.

* * * * *